(12) United States Patent
Sutherland et al.

(10) Patent No.: US 11,890,193 B2
(45) Date of Patent: Feb. 6, 2024

(54) SYSTEM AND METHOD FOR REDUCING TRICUSPID REGURGITATION

(71) Applicant: Edwards Lifesciences Corporation, Irvine, CA (US)

(72) Inventors: Michael W. Sutherland, Pelham, NH (US); Steven D. Cahalane, Pelham, NH (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 277 days.

(21) Appl. No.: 17/083,127

(22) Filed: Oct. 28, 2020

(65) Prior Publication Data

US 2021/0038378 A1 Feb. 11, 2021

Related U.S. Application Data

(62) Division of application No. 15/393,809, filed on Dec. 29, 2016, now Pat. No. 10,828,160.

(Continued)

(51) Int. Cl.
*A61F 2/24* (2006.01)
*A61B 17/04* (2006.01)
*A61B 17/00* (2006.01)

(52) U.S. Cl.
CPC .......... *A61F 2/246* (2013.01); *A61B 17/0401* (2013.01); *A61F 2/2451* (2013.01);
(Continued)

(58) Field of Classification Search
CPC ...... A61F 2/246; A61F 2/2451; A61F 2/2466; A61B 17/0401; A61B 2017/00867;
(Continued)

(56) References Cited

U.S. PATENT DOCUMENTS 3,604,488 A 9/1971 Wishart et al.
3,656,185 A 4/1972 Carpentier
(Continued)

FOREIGN PATENT DOCUMENTS

CN 113331995 A 9/2021
EP 1034753 A1 9/2000
(Continued)

OTHER PUBLICATIONS

Agarwal et al. International Cardiology Perspective Functional Tricuspid Regurgitation, Circ Cardiovasc Interv 2009:2;2;565-573 (2009).
(Continued)

*Primary Examiner* — Sarah A Long
(74) *Attorney, Agent, or Firm* — Anya Adams

(57) ABSTRACT

A first anchor is anchored inside a coronary sinus of a heart of a subject. A second anchor can be driven into a tricuspid annulus of the heart. A distal portion of the second anchor can be disposed adjacent and parallel to a center portion of the second anchor. The second anchor can be seated against a surface of the annulus, for example, such that (i) the distal portion is disposed perpendicular to the center portion, (ii) the center portion extends through the annulus, and (iii) a proximal portion of the second anchor is disposed in the atrium. A distance between the first and second anchors can be reduced by applying tension to a tensioning member coupled to the first anchor and the proximal portion of the second anchor. Other embodiments are also described.

19 Claims, 10 Drawing Sheets

Related U.S. Application Data

(60) Provisional application No. 62/272,871, filed on Dec. 30, 2015.

(52) U.S. Cl.
CPC ............ *A61B 2017/00867* (2013.01); *A61B 2017/0409* (2013.01); *A61B 2017/0414* (2013.01); *A61B 2017/0417* (2013.01); *A61B 2017/0445* (2013.01); *A61B 2017/0464* (2013.01); *A61B 2017/0496* (2013.01); *A61F 2/2466* (2013.01)

(58) Field of Classification Search
CPC .... A61B 2017/0409; A61B 2017/0414; A61B 2017/0417; A61B 2017/0464; A61B 2017/0496
See application file for complete search history.

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavonik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |

(56) References Cited

U.S. PATENT DOCUMENTS

| | | |
|---|---|---|
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |

(56) References Cited

U.S. PATENT DOCUMENTS

| | | |
|---|---|---|
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,724,084 B2 | 8/2017 | Groothuis et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083538 A1 | 5/2003 | Adams et al. |
| 2003/0093148 A1 | 5/2003 | Bolling et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |

(56) References Cited

U.S. PATENT DOCUMENTS

| | | |
|---|---|---|
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0049211 A1 | 3/2004 | Tremulis et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |

(56) References Cited

U.S. PATENT DOCUMENTS

| | | |
|---|---|---|
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0228223 A1 | 9/2008 | Alkhatib |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung |
| 2009/0088837 A1 | 4/2009 | Gillinov et al. |
| 2009/0093670 A1* | 4/2009 | Annest ............... A61B 17/0401 606/139 |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144576 A1 | 6/2011 | Rothe et al. |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0018459 A1* | 1/2013 | Maisano ............ A61B 17/0401 623/2.37 |
| 2013/0030522 A1 | 1/2013 | Rowe et al. |

(56) References Cited

U.S. PATENT DOCUMENTS

| | | |
|---|---|---|
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0103055 A1 | 4/2013 | Schaller et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350657 A1* | 11/2014 | Headley ............... A61F 2/91 623/1.15 |
| 2014/0350660 A1 | 11/2014 | Cocks et al. |
| 2014/0379006 A1 | 12/2014 | Sutherland et al. |
| 2015/0018940 A1* | 1/2015 | Quill ............... A61F 2/2442 623/2.11 |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0119936 A1* | 4/2015 | Gilmore ............. A61B 17/0401 606/232 |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0256149 A1 | 9/2016 | Sampson et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0159898 A1 | 5/2019 | Kutzik et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015971 A1 | 1/2020 | Brauon et al. |
| 2020/0289267 A1 | 9/2020 | Peleg et al. |
| 2020/0337840 A1 | 10/2020 | Reich |
| 2021/0015475 A1 | 1/2021 | Lau |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2021/0145584 A1 | 5/2021 | Kasher et al. |
| 2022/0000464 A1 | 1/2022 | Schaller et al. |
| 2022/0071620 A1 | 3/2022 | Brauon et al. |
| 2022/0096232 A1 | 3/2022 | Skaro et al. |
| 2022/0142779 A1 | 5/2022 | Sharon |
| 2022/0176076 A1 | 6/2022 | Keidar |
| 2022/0233316 A1 | 7/2022 | Sheps et al. |
| 2022/0273436 A1 | 9/2022 | Aviv et al. |
| 2022/0313438 A1 | 10/2022 | Chappel-Ram |
| 2022/0323221 A1 | 10/2022 | Sharon et al. |
| 2023/0016867 A1 | 1/2023 | Tennenbaum |

FOREIGN PATENT DOCUMENTS

| | | |
|---|---|---|
| EP | 3531975 A1 | 9/2019 |
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2007098512 A1 | 9/2007 |
| WO | 2010000454 A1 | 1/2010 |
| WO | 2012176195 A3 | 3/2013 |
| WO | 2014064964 A1 | 5/2014 |
| WO | 2015063580 A2 | 5/2015 |
| WO | 2019145941 A1 | 8/2019 |
| WO | 2019145947 A1 | 8/2019 |
| WO | 2019182645 A1 | 9/2019 |

(56) References Cited

FOREIGN PATENT DOCUMENTS

| | | |
|---|---|---|
| WO | 2019224814 A1 | 11/2019 |
| WO | 2020240282 A2 | 12/2020 |
| WO | 2021014440 A2 | 1/2021 |
| WO | 2021038559 A1 | 3/2021 |
| WO | 2021038560 A1 | 3/2021 |
| WO | 2022064401 A2 | 3/2022 |
| WO | 2022090907 A1 | 5/2022 |
| WO | 2022101817 A2 | 5/2022 |
| WO | 2022153131 A1 | 7/2022 |
| WO | 2022157592 A1 | 7/2022 |
| WO | 2022172108 A1 | 8/2022 |
| WO | 2022172149 A1 | 8/2022 |
| WO | 2022200972 A1 | 9/2022 |
| WO | 2022224071 A1 | 10/2022 |
| WO | 2022229815 A1 | 11/2022 |
| WO | 2022250983 A1 | 12/2022 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon 36.06 (1988): 313-319.

Ahmadi, Ali et al. "Percutaneously adjustable pulmonary artery band." The Annals of thoracic surgery 60 (1995): S520-S522.

Alfieri et al. "Novel Suture Device for Beating-Heart Mitral Leaflet Approximation", Ann Thorac Surg. 2002, 74:1488-1493.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

Amplatzer® Cribriform Occluder. A patient guide to Percutaneous, Transcatheter, Atrial Septal Defect Closuer, AGA Medical Corporation, Apr. 2008.

Amplatzer® Septal Occluder. A patient guide to the Non-Surgical Closure of the Atrial Septal Defect Using the Amplatzer Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success—midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology 52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. Ring+String, Successful Repair technique for ischernic mitral regurgitation with severe leaflet Tethering, The Department of Thoracic Cardiovascular surgery, Hamburg, Germany, Nov. 2008.

Maisano, "The double-orifice technique as a standardized approach to treat mitral," European Journal of Cardio-thoracic Surgery 17 (2000) 201-205.

O'Reilly S et al., "Heart valve surgery pushes the envelope," Medtech Insight 8(3): 73, 99-108 (2006).

Odell JA et al., "Early Results o4yf a Simplified Method of Mitral Valve Annuloplasty," Circulation 92:150-154 (1995).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology, 15(5), pp. 389-391.

Swenson, Orvar. "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

\* cited by examiner

SYSTEM AND METHOD FOR REDUCING TRICUSPID REGURGITATION

CROSS REFERENCE TO RELATED APPLICATION

The present application is a divisional of U.S. Ser. No. 15/393,809 to Sutherland et al., filed Dec. 29, 2016, which claims priority to U.S. patent application Ser. No. 62/272,871, filed Dec. 30, 2015. The foregoing applications are hereby incorporated by reference herein in their entirety.

TECHNICAL FIELD

The present teachings generally relate to tissue anchor systems and uses thereof in treating tricuspid regurgitation.

BACKGROUND

Tricuspid valve diseases relate to conditions in which the valve between the two right heart chambers (i.e., the right ventricle and the right atrium) doesn't function properly and these diseases often occur with other heart valve problems. Examples of tricuspid valve diseases include tricuspid valve regurgitation, tricuspid valve stenosis, tricuspid valve atresia, and the Ebstein's anomaly. In the tricuspid valve regurgitation, the tricuspid valve doesn't close properly and blood flows back into the right atrium; in the tricuspid valve stenosis, the tricuspid valve is narrowed and reduces the amount of blood flowing into the right ventricle; in the tricuspid atresia, a congenital heart disease, a solid wall of tissues blocks the blood from flowing between the two right heart chambers; and in the Ebstein's anomaly, a malformed tricuspid valve situates at a position lower than the normal position in the right ventricle and causes blood to flow back into the right atrium. There are other tricuspid valve diseases generally known to a person with ordinary skill in the art and these tricuspid valve diseases are also included in the present teachings.

A tricuspid valve disease can be corrected by an annuloplasty ring. In some instances, this device is preferred for surgically repairing a defective tricuspid valve. An annuloplasty ring is an anatomically-correct three-dimensional (3D) ring and can flexibly conform to the heart valve opening. This ring is implanted into a defective tricuspid valve and reduces the valve opening. Properly implanted, an annuloplasty ring allows the valve to open and close properly.

Tricuspid valve repair surgeries can be done in one of the following two ways: a minimally invasive surgery or an open-heart surgery. A minimally invasive method involves making a small incision in the upper or lower chest and inserting a valve repairing system/device percutaneously. After the valve is repaired, the incision may be closed with dissolving sutures. In some minimally invasive techniques the initial incision or puncture can be allowed to heal without sutures. In this event any bleeding is stopped with manual compression following the procedure. Comparing to an open-heart surgery, advantages of a minimally invasive approach include a shorter recovery time, less post-operation pain, and earlier return to work and normal daily activities.

However, there are drawbacks in either procedures and therefore needs still exist for repairing a diseased tricuspid valve with alternative approaches.

SUMMARY

One aspect of the present teachings provides a percutaneous repair system for reducing a tricuspid annulus circumference. The system comprises a first anchor configured to be deployed inside the coronary sinus, and a second anchor configured to be deployed across the tricuspid annulus. The system further comprises a first tensioning member configured to apply tension to the first anchor with a fixed end connecting to the first anchor and a free end; and a second tensioning member configured to apply tension to the second anchor with a fixed end connecting to the second anchor, and a free end. The system further comprises a lock member joining the free ends of both first and second tensioning members. The lock member is configured to maintain the tension on both the anchors.

Another aspect of the present teachings provides a percutaneous repair system for reducing a tricuspid annulus circumference. The system comprises a first anchor configured to be deployed inside the coronary sinus, and a second anchor configured to be deployed across the tricuspid annulus. The system further comprises a first tensioning member configured to apply tension to the first anchor with a first end connecting to the first anchor and a second end joining a lock member. The second anchor is configured to slide over the first tensioning member. The first tensioning member is configured to apply tension to the first anchor, and the lock member is configured to maintain the tension.

Another aspect of the present teachings provides a percutaneous repair system for reducing a tricuspid annulus circumference. The system comprises a first anchor configured to be deployed inside the coronary sinus and a second anchor configured to be deployed across the tricuspid annulus. The system further comprises a first distance between the first and second anchors and a second reduced distance between the first and second anchors.

Another aspect of the present teachings provides a method for percutaneously reducing the circumference of a tricuspid annulus. This method comprises implanting a first anchor into the coronary sinus and implanting a second anchor across the tricuspid annulus. In various embodiments, each of the first and second anchors connects to a tensioning member. The method further comprises applying tension to both the tensioning members so as to reduce the distance between the first and second anchors from a first distance to a second distance. The method further comprises implanting a locking member to secure the second distance between the first and second anchors. The method further comprises reducing the circumference of the tricuspid valve by tensioning both the tensioning members.

DETAILED DESCRIPTION

Figure 1:
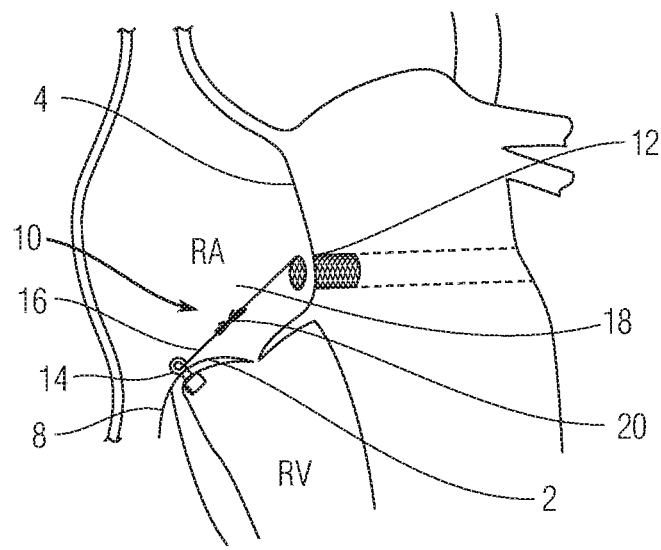
FIG. 1 is a perspective view of an embodiment of the present teachings where a vascular anchor and an annulus anchor deployed at a treatment location, and tension is applied to both the anchors deployed across the tricuspid annulus in accordance with the present teachings.

Certain specific details are set forth in the following description and figures to provide an understanding of various embodiments of the present teachings. Those of ordinary skill in the relevant art would understand that they can practice other embodiments of the present teachings without one or more of the details described herein. Thus, it is not the intention of the Applicant(s) to restrict or in any way limit the scope of the appended claims to such details. While various processes are described with reference to steps and sequences in the following disclosure, the steps and sequences of steps should not be taken as required to practice all embodiments of the present teachings.

As used herein, the term "lumen" means a canal, a duct, or a generally tubular space or cavity in the body of a subject, including a vein, an artery, a blood vessel, a capillary, an intestine, and the like. The term "lumen" can also refer to a tubular space in a catheter, a sheath, a hollow needle, a tube, or the like.

As used herein, the term "proximal" shall mean close to the operator (less into the body) and "distal" shall mean away from the operator (further into the body). In positioning a medical device inside a patient, "distal" refers to the direction away from a catheter insertion location and "proximal" refers to the direction close to the insertion location.

As used herein, the term "wire" can be a strand, a cord, a fiber, a yarn, a filament, a cable, a thread, or the like, and these terms may be used interchangeably.

As used herein, the term "sheath" may also be described as a "catheter" and, thus, these terms can be used interchangeably.

Unless otherwise specified, all numbers expressing quantities, measurements, and other properties or parameters used in the specification and claims are to be understood as being modified in all instances by the term "about." Accordingly, unless otherwise indicated, it should be understood that the numerical parameters set forth in the following specification and attached claims are approximations. At the very least and not as an attempt to limit the application of the doctrine of equivalents to the scope of the attached claims, numerical parameters should be read in light of the number of reported significant digits and the application of ordinary rounding techniques.

The present teachings relate to devices and methods for treating a tricuspid valve regurgitation percutaneously. Although referring to FIGS. 1 to 19, a person with ordinary skill in the art would recognize that the figures and description thereto refer to various embodiments of the present teachings and, unless indicated otherwise by their contexts, do not limit the scope of the attached claims.

An aspect of the present teachings relates to methods of reducing the circumference of a tricuspid valve (2). For example, now referring to FIG. 1, the circumference of a tricuspid valve (2) can be reduced by deploying an anchoring system (10) with a vascular anchor (12) deployed inside the coronary sinus and an annulus anchor (14) engaging at a location along the anterior or posterior annulus. Each anchor is attached with a flexible tensioning member (16, 18). Tension is then applied to both the anchors, and a lock member (20) secures free ends of both the flexible tensioning members (16, 18) while maintaining the tension at a pre-defined level. Upon deployment of this anchor system (10), the tricuspid annulus (8) is pulled toward the inferior portion of the atrial septum (4). Depending on the location of the annulus anchor (14), a portion of the annulus could fold. Alternatively, the overall shape of the annulus could change. Both the results would lead to more coaptation of the tricuspid leaflets and, therefore, reduce or eliminate the tricuspid valve regurgitation jet. As a result, the tricuspid valve (2) could be fully closed during a right ventricular systole.

Figure 2:
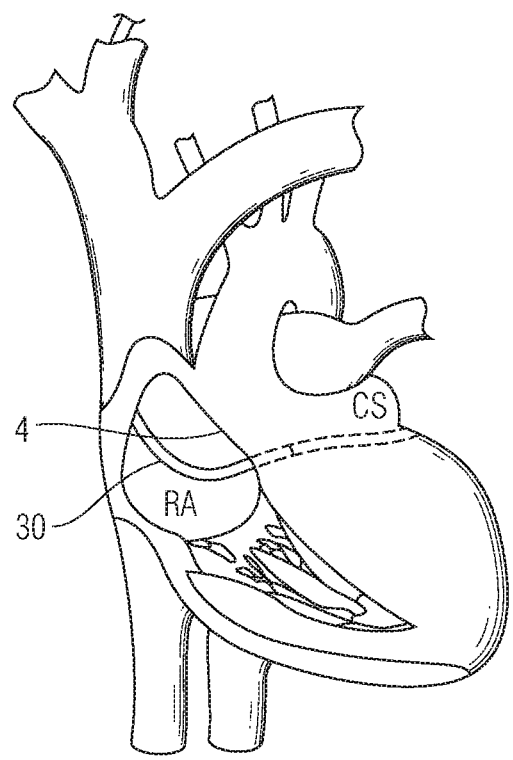
FIG. 2 is a perspective view of an exemplary vascular anchor delivery system percutaneously inserted into the coronary sinus in accordance with the present teachings.
Figure 3A:
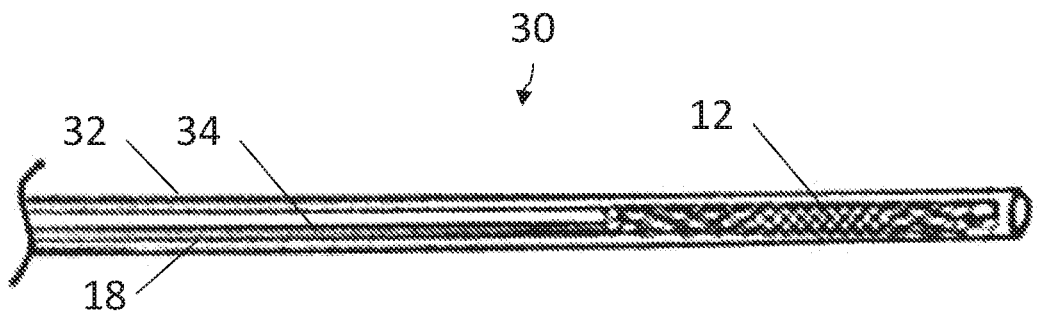
FIGS. 3A-3B are embodiments of an exemplary vascular anchor (12) in its delivery profile and attached to a delivery system in accordance with the present teachings.
Figure 3B:
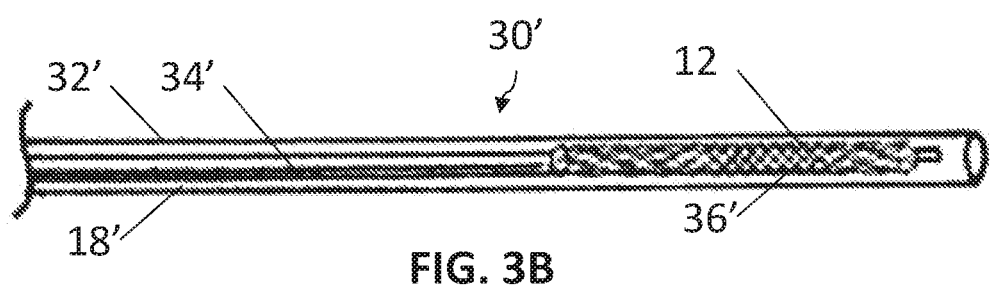
Figure 4:
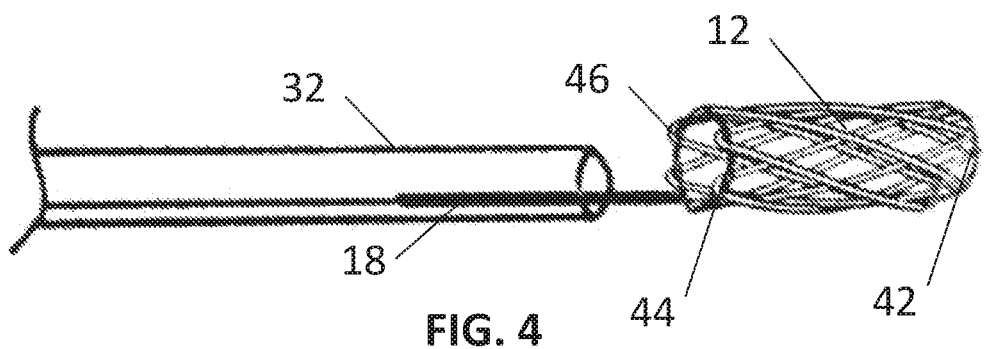
FIG. 4 is an embodiment of an exemplary vascular anchor in its deployed profile in accordance with the present teachings.

FIGS. 2-4 illustrate the deployment of a vascular anchor (12) inside the coronary sinus (CS) according to the present teachings. According to some embodiments, a vascular anchor delivery system (30) gains access through a standard right heart catheterization procedure, for example, through the femoral vein, the inferior vena cava, and the right atrium. Once inside the right atrium, the vascular anchor delivery system (30) extends further through the opening of the coronary sinus at the inferior portion of the atrial septum (4). In one embodiment, the vascular anchor (12) is then deployed inside the coronary sinus, 15-25 mm from its right atrium opening.

FIG. 2 illustrates an alternative embodiment of delivering a vascular anchor (12) inside the coronary sinus. In this embodiment, the access to the right atrium is gained by entering the jugular vein; extending through the right brachiocephalic vein and the superior vena cava (6); and reaching the right atrium. Once inside the right atrium, the delivery system further extends downwardly towards the inferior region of the atrial septum (4), and enters the opening of the coronary sinus. Similarly, once inside, a vascular anchor (12) is then deployed inside the coronary sinus.

Figure 5:
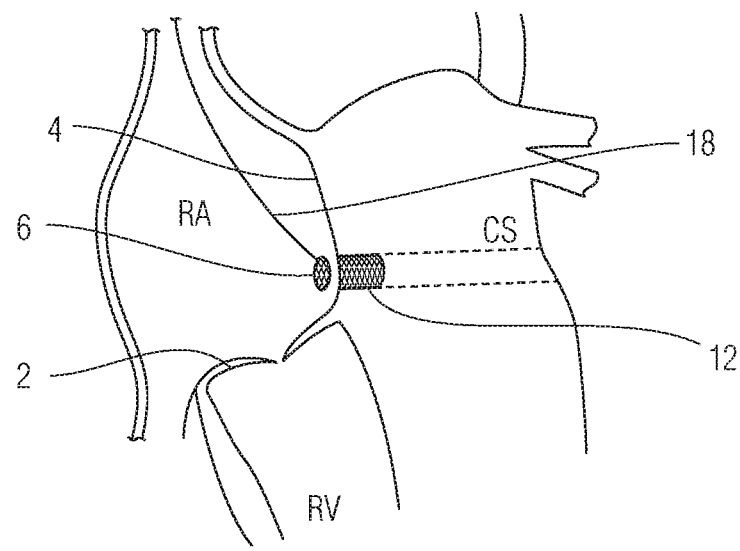
FIG. 5 is a perspective view of an exemplary vascular anchor deployed inside the coronary sinus in accordance with the present teachings.

FIG. 5 illustrates a vascular anchor (12) deployed inside the coronary sinus, where the vascular anchor (12) secures itself to its surrounding tissue, and the vascular anchor (12) connects to a flexible tensioning member (18) which extends proximally outside of the coronary sinus. As shown in FIG. 5, a portion of the flexible tensioning member (18) is inside the right atrium, and the flexible tensioning member (18) further extends proximally with its proximal end extending outside of the body.

FIGS. 3-4 further illustrate an embodiment of the delivery system (30, 30'). The delivery system (30, 30') includes a delivery sheath (32, 32') that holds a vascular anchor (12) in its delivery profile. The delivery system (30, 30') could further includes a mechanism (34, 34') that can be used to transport a vascular anchor (12), for example from the proximal end of the delivery sheath (32, 32') to the distal end of the delivery sheath (32, 32'), or push the vascular anchor (12) distally out of the distal end of the delivery sheath (32, 32').

According to some embodiments of the present teachings, the vascular anchor (12) deployed inside the coronary sinus has an elongated body which is suitable for being positioned inside the vasculature. In some embodiments, the vascular anchor (12) is configured to collapse into a radially profile which is suitable to be delivered percutaneously by a delivery system (30, 30') as described above, for example, as shown in FIGS. 3A-3B. In some embodiments, the vascular anchor (12) expands radially during the deployment. In some embodiments, as the vascular anchor (12) expands radially, the overall longitudinal length of the vascular anchor (12) shortens, for example, as shown in FIG. 4.

In some embodiments, the vascular anchor (12) is to be delivered through a vascular anchor delivery mechanism (34, 34'). The delivery mechanism (34, 34') is designed to engage the vascular anchor (12) during its delivery, which allows the vascular anchor (12) to be pushed distally, pulled proximally, or held steady while the vascular anchor (12) transitions from its collapsed delivery profile into its radially expanded deployed profile. The engagement between the delivery mechanism (34, 34') and the vascular anchor (12) is configured to be detachable, for example, at the distal end (42) of the vascular anchor (12), at the proximal end (44) of the vascular anchor (12), or through a central lumen (46) of the vascular anchor (12). The connecting flexible tensioning member (18) is configured to be disposed inside the delivery mechanism (34, 34'), or alternatively, along the delivery mechanism (34, 34') while locating inside the delivery sheath (32, 32').

In some embodiments, the vascular anchor (12) is made from a super-elastic or shape-memory material such as Nitinol. The super-elastic material would allow the vascular anchor (12) to be advanced to the implantation site in a collapsed configuration. Simply unsheathing the vascular anchor (12) could then allow the vascular anchor (12) to expose, expand, and contact the walls of the vasculature, for example, the coronary sinus. According to one embodiment of the present teachings, as shown in FIG. 3A, the delivery system (30) includes an outer sheath (32) and an inner catheter (34) which resides inside the lumen of the outer sheath (32). The inner catheter (34) resides inside the collapsed lumen of the vascular anchor (12) and is configured to engage the vascular anchor (12) when the vascular anchor (12) is in its collapsed state by a known mechanism to those skilled in the field, such as a simple hook or groove mechanism. In some embodiments (not shown), the inner catheter (34) features an inner lumen which is configured to allow a positioning wire to pass through the inner lumen. In some embodiments, the inner lumen of the inner catheter (34) is configured to allow a 0.3-0.9 mm interventional wire to pass through. Optionally, the positioning wire is configured to locate the coronary sinus. A vascular delivery system (30) then tracts over the positioning wire to the intended treatment location.

In other embodiments, the vascular anchor (12) is made of a plastically deformable material such as stainless steel, cobalt chromium, or similar materials. In some embodiments, the vascular anchor (12) is made from a polymeric material such as PET or other plastically deformable material. In some embodiments, the deformable anchor (12) includes a collapsed deployment configuration and an expanded implanting configuration. In the collapsed deployment configuration, the anchor (12) is collapsed around a deflated endovascular balloon, as shown in FIG. 3B. The endovascular balloon may be made of any of the materials known to one with ordinary skill in the current state of the art, including PET or Mylar, polyurethane, or similar materials. In some embodiments (not shown in FIG. 3B), the endovascular balloon is defined by an annular inflation space with an internal diameter that is configured to allow passage of an interventional wire. In some embodiments, the vascular anchor (12) is collapsed on the annular balloon and held in a collapsed state by an outer sheath (32'). The delivery system (30') including the outer sheath (32'), the annular balloon (36') and a balloon catheter (34'), the vascular anchor (12), and the positioning wire is delivered into the coronary sinus. (Similar to descried above, the positioning wire is used to locate the coronary sinus.) Once the vascular anchor is implanted, the outer sheath (32') is removed or partially retracted, exposing the vascular anchor (12), along with the inflation balloon (36'). The balloon is then inflated, causing the vascular anchor (12) to deform, expand, and engage the inner surface of the vasculature.

As shown in FIG. 4, according to some embodiments, the vascular anchor (12) has a generally tubular profile with a hollow surface structure, which allows an easy radial expansion of the vascular anchor (12) during the deployment. The vascular anchor (12) includes a distal end (42), a proximal end (44), and a longitudinal lumen (46), which does not impede blood flow.

According to some embodiments, the overall length of the vascular anchor (12) in its deployed profile is 15-25 mm. According to some embodiments, the general size of the vascular anchor (12) is 12-18 mm in diameter. According to some embodiments, the vascular anchor (12) has a generally tubular deployed profile. In another embodiment, the vascular anchor (12) has a conical or frustro-conical deployed configuration with its proximal end having a larger general diameter, and the distal end having a relatively smaller diameter. One skilled in the art should understand that the overall size of a vascular anchor (12) is designed for even distribution of the force to the surrounding tissue. As a result, it could vary based on an individual patient.

In another embodiment, the proximal end of the anchor is positioned approximately to the ostium (6) of the coronary sinus. In another embodiment, the proximal end of the vascular anchor (12) is positioned significantly into the coronary sinus. In a particular embodiment, the vascular anchor (12) is advanced until it resides along the posterior aspect of the left heart approximately 20-80 mm into the coronary sinus, for example the proximal end of the anchor is positioned 15 mm from the ostium and inside the coronary sinus A clinician should determine the optimum implantation location based on each patient's symptom and anatomy. Thus, what has been disclosed here is merey an example, and should not be viewed as limiting.

In some embodiments of the present teachings, the vascular anchor (12) has a hollow surface structure along its tubular surface. As illustrated, each hollowed surface structure is separated by struts with wavy or zigzag patterns. A wavy and zigzag pattern allows the tubular body of the anchor to expand radially. According to some embodiments, the vascular anchor (12) with a hollow surface structure is fabricated by laser-cutting or acid-etching a pattern into a preformed tube, then shape-setting the anchor to the intended deployed configuration. In such embodiments, the vascular anchor (12) with a hollow surface structure is formed by slotting a hollow tube, for example, with a machining laser, a water drill, or other methods, and expanding the slotted hollow tube to form an open structure. Alternatively, a vascular anchor (12) with a hollow surface structure can be formed with a woven, knitted, or braided tubular metallic fabrics made out of metallic strands. The term "strand" used herein can be wires, cords, fibers, yarns, filaments, cables, threads, or the like, and these terms may be used interchangeably.

A vascular anchor (12) of the present teachings is configured to engage the surrounding tissues when the vascular anchor (12) is deployed. According to one embodiment, once exiting from the delivery sheath, the vascular anchor (12) expands radially so that it secures itself to the surrounding tissues. In some embodiments, the vascular anchor (12) is made of a thermal shape memory material so that once exposed inside the blood stream, the vascular anchor (12) expands radially by itself. In another embodiment, the vascular anchor (12) is expanded by a vascular balloon.

Once deployed inside a vasculature, the vascular anchor (12) expands and secures itself at a location inside the coronary sinus without migrating along the length of the vein. In some embodiments, the vascular anchor (12) secures to the surrounding tissues through interference between its tubular surface and the vasculature. In another embodiment, the vascular anchor (12) has tissue engagement features such as barbs, hooks. In some embodiments, the vascular anchor (12) is designed to locally expand the coronary sinus significantly. In some embodiments, the vascular anchor (12) when deployed causes the internal diameter of the vascular anchor (12) to increase by 50%. Due to the anatomical structure of the heart, it is sometimes preferred that the tissue engagement feature is oriented facing inward of the heart.

In some embodiments, the vascular anchor (12) is configured to engage the internal diameter of the coronary sinus near the coronary sinus ostium (6). In some embodiments, the vascular anchor (12) is configured to engage the Eustachian valve near the coronary sinus ostium (6). In some embodiments, the vascular anchor (12) completely punctures the ridge of tissue separating the coronary sinus ostium (6) from the right atrium. This ridge of tissue may be referred to as a Eustachian valve. In patients with significant tricuspid regurgitation, this tissue ridge is often enlarged or at least more pronounced by the dilation of the surrounding heart chambers. In yet other embodiments, the vascular anchor (12) is implanted into one of the venous branches extending from the coronary sinus.

As shown in FIG. 5, the deployed vascular anchor (12) is attached with a flexible tensioning member (18). The distal end of the flexible tensioning member (18) joins the vascular anchor (12). The proximal end of the flexible tensioning member (18) extends proximally and eventually exits to the outside of the body and remains in the control of a clinician. As shown in FIG. 5, before the treatment is completed, a portion of the flexible tensioning member (18) is exposed inside the right atrium. According to some embodiments, the flexible tensioning member (18) attaches to a proximal end of the vascular anchor (12). According to an alternative embodiment, the flexible tensioning member (18) attaches to any portion of the anchor. One skilled in the art should understand that the connection between the flexible tensioning member (18) and the vascular anchor (12) should be strong enough to withstand a certain amount of strain applied later. In some embodiments the vascular anchor (12) is made from a laser cut Nitinol tube which has been formed into a stent-like structure. An eyelet may be cut into the stent like structure, allowing the attachment of a suture material to the eyelet by a simple knot. In other embodiments, a suture is attached to the vascular anchor (12) by swaging, crimping, gluing, pinching, or clamping the suture to a feature of the vascular anchor (12).

FIG. 5 illustrates an embodiment of the present teachings, where the flexible tensioning member (18) attachment point is at or approximately to the ostium (6) of the coronary sinus. As shown, the flexible tensioning member (18) attaches to the vascular anchor (12) on its outside edge of the curve, further away from the tricuspid valve.

Figure 6:
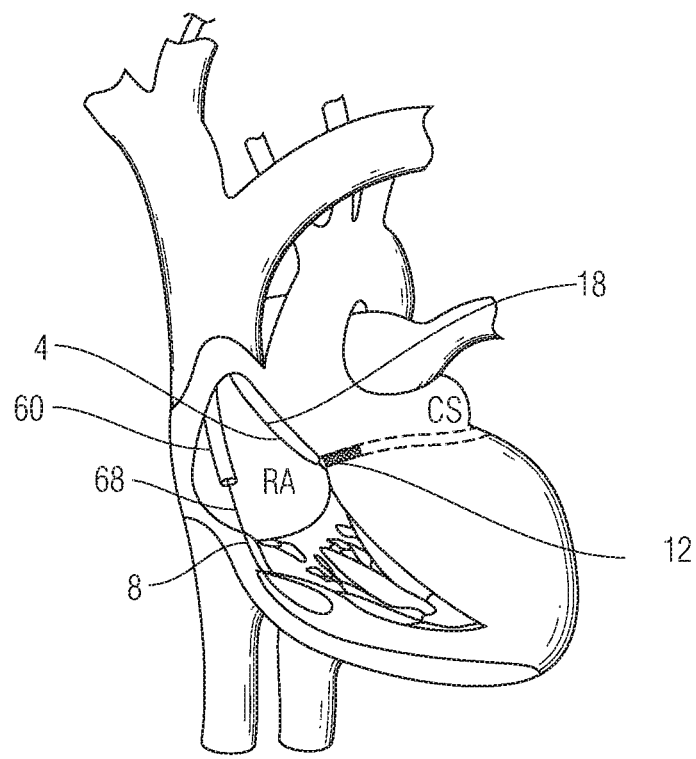
FIG. 6 is a perspective view of an exemplary wire positioned across the annulus in accordance with the present teachings.
Figure 7:
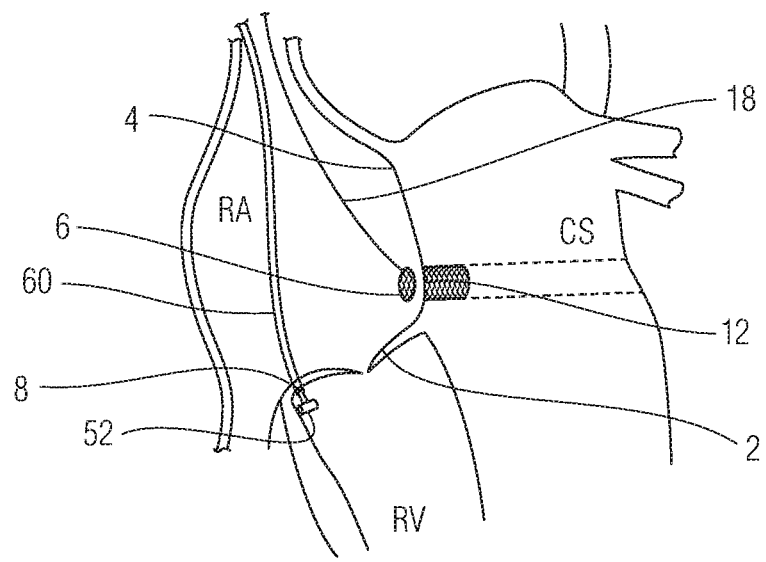
FIG. 7 is a perspective view of an exemplary annulus anchor deployed inside the right ventricle in accordance with the present teachings.
Figure 8:
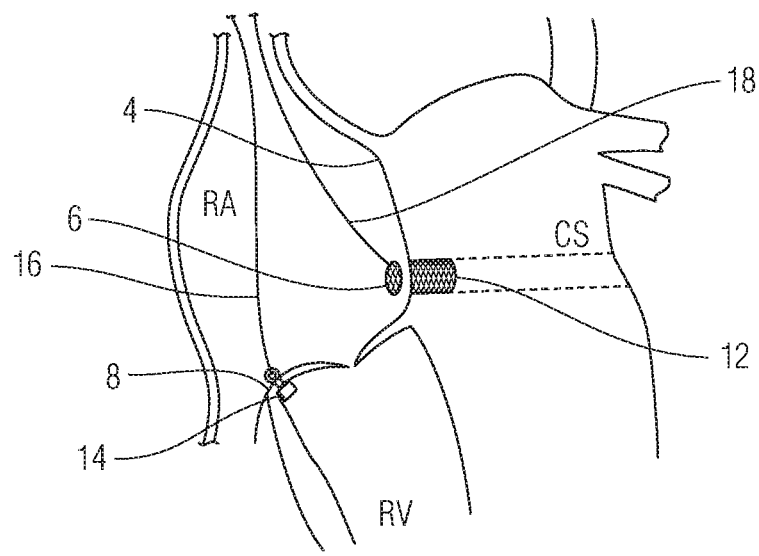
FIG. 8 is an embodiment of an exemplary annulus anchor in its deployed profile in accordance with the present teachings.

Now referring to FIGS. 6-8, where an annulus anchor (14) is deployed at a location along the tricuspid annulus (8). As shown in FIG. 8, the annulus anchor (14) has a distal portion (52), which is deployed against the right ventricle side of the annulus, a center portion (54), which is positioned through the annulus (8), and a proximal portion (56), which is positioned inside the right atrium. A second flexible tensioning member (16) attaches to the proximal portion of the annulus anchor (14). The flexible tensioning member (16) also has a distal end attaching to the annulus anchor (14), and a proximal end that extends proximally through the annulus anchor delivery system (60) and eventually outside of the body, and remains in control by a clinician. As shown in FIG. 8, once the annulus anchor (14) is deployed at a treatment location, a portion of the second flexible tensioning member (16) is exposed inside the right atrium.

Deployment of the annulus anchor (14) starts with an annulus anchor delivery system (60) gaining access to the right atrium. FIG. 6 illustrates an embodiment where the access to the right atrium is gained by the annulus anchor delivery system (60) entering the jugular vein, and extending through the right brachiocephalic vein and the superior vena cava, and reaching the right atrium. Alternative accesses to the right atrium could be gained through a standard right heart catheterization procedure, similar to those described above, for example, with the delivery system entering through the femoral vein, the inferior vena cava, and the right atrium.

Once inside the right atrium, the annulus anchor delivery system (60) further extends downwardly towards the tricuspid annulus (8). After an implant location is identified, a locating wire (68) punctures the annulus (8) to create an aperture. A tissue anchor is deployed at the location. Methods of locating and placing a locating wire (68) at a selected implant location is disclosed in U.S. patent application Ser. No. 14/190,732 (now U.S. Pat. No. 9,724,084), filed on Feb. 26, 2014, entitled "Devices and Methods for Percutaneous Tricuspid Valve Repair," the content of which is incorporated by reference herein in its entirety.

Once an implant location is identified and marked with a locating wire (68), as shown in FIG. 6, a locating wire (68) extends from the right atrium, across the tricuspid annulus (8), and into the right ventricle. An annulus anchor (14) is then deployed across the aperture created by the locating wire (68). Unlike the deployment of the vascular anchor (12), the annulus anchor (14) is deployed in a step-wise process. As the distal end of the annulus anchor delivery system (60) extends through the aperture into the right ventricle, the distal end of the annulus anchor (14) is pushed outside of the distal end of the annulus anchor delivery system (60). The distal portion (52) of the annulus anchor (14) assumes its radially expanded profile, as shown in FIG. 7. The delivery system holds the rest of the annulus anchor (14), then is pulled proximally so that the distal portion (52) of the annulus anchor (14) is positioned against the annulus tissue. The delivery system (60) is then pulled further proximally to expose the center portion (54) of the annulus anchor (14), and the proximal portion (56) of the annulus anchor (14).

Figure 9A:
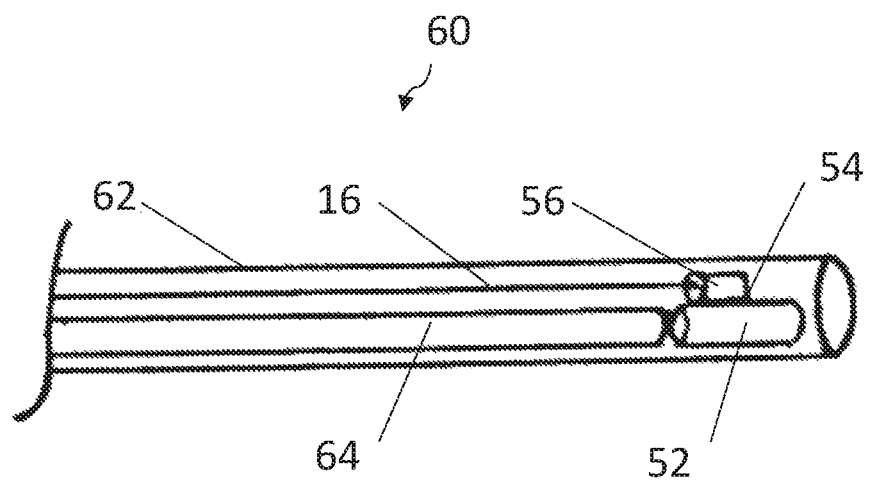
FIG. 9A is an embodiment of an exemplary annulus anchor in its delivery profile and attached to a delivery system in accordance with the present teachings.
Figure 9B:
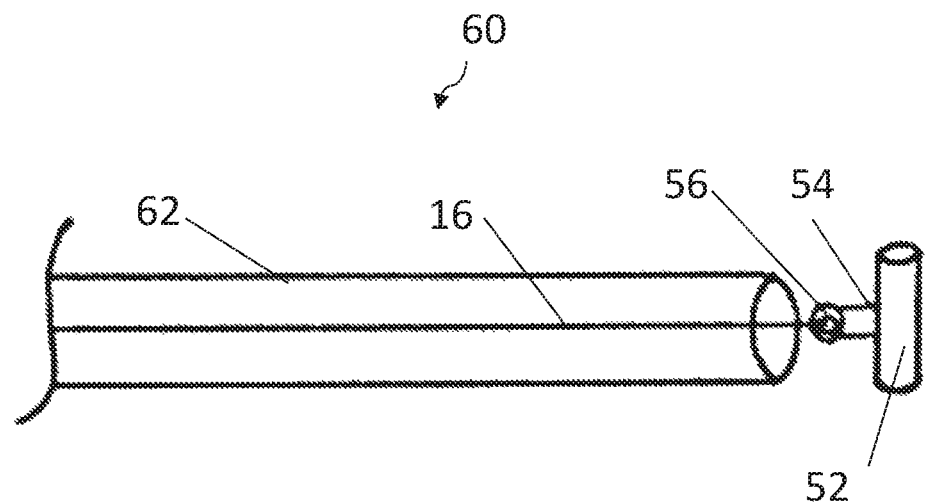
FIG. 9B is an embodiment of an exemplary annulus anchor in its deployed profile in accordance with the present teachings.

FIGS. 9A-9B illustrate an embodiment of an annulus anchor (14) of the present teachings. As shown in FIG. 9B, the annulus anchor (14) has a large elongated distal portion (52), which is designed to be pivotable at the location where it joins the center portion (54) of the annulus anchor (14). During delivery (as shown in FIG. 9A), the distal portion (52) of the anchor (14) pivots radially so that it aligns with the center portion (54) of the anchor (14). The entire annulus anchor (14) is configured to be slidably disposed inside the delivery sheath (62). FIG. 9A further illustrates that the annulus anchor delivery system (60) also includes an outer sheath (62) and an inner catheter (64) which resides inside the lumen of the outer sheath (62). The distal end of the inner catheter (64) contacts the annulus anchor (14) and is configured to push the annulus anchor (14) distally, or prevent annulus anchor (14) from sliding proximally inside the delivery sheath (62). According to some embodiments, simply unsheathing the delivery sheath (62), or pushing the delivery catheter (64) distally while holding the delivery sheath (62) steady allows the annulus anchor (14) to be exposed and expand.

According to some embodiments, upon deployment, the distal portion (52) of the annulus anchor (14) pivots automatically and assumes its profile perpendicular to the center portion (54) of the anchor (14), as shown in FIG. 9B. Upon deployment, the distal portion (52) of the annulus anchor (14) is positioned against the ventricular side of the annulus. According some embodiments of the present teachings, the deployed annulus anchor (14) is deployed at the anterior-posterior commissure or 3 mm in each direction of this commissure.

The center portion (54) of the annulus anchor (14) also has an elongated profile. The center portion (54) of the annulus anchor (14) pivotably joins the distal portion (52) of the anchor (14), and, in some embodiments, pivotably attaches to the proximal portion (56) of the anchor (14). As shown in FIG. 9A, during delivery, the center portion (54) of the anchor (14) aligns with the distal portion (52) of the anchor (14), and is slidably disposed inside the delivery sheath (62). During deployment, at least a portion of, sometimes the entire, center portion (54) of the annulus anchor (14) is also deployed along with the distal portion (52) of the anchor. Specifically, as the delivery system (60) is pulled back proximally, and the distal portion (52) of the anchor (14) is positioned against the annulus, the center portion (54) of the anchor (14) is positioned through the aperture across the annulus (8).

According to some embodiments, the proximal portion (56) of the anchor (14) is an extension of the center portion (54) of the anchor (14). Thus, the connection between the center portion (54) and the proximal portion (56) is rigid. One skilled in the art should understand, for example, that the proximal portion (56) of the anchor (14) can adopt other profiles, for example, those similar to the profiles of the distal portion (52). Once released from the delivery system (60), the proximal portion (56) of the annulus anchor (14) can also pivot and assume its expanded profile, sometimes similar to the distal portion (52) of the annulus anchor (14).

Many other shapes and profiles could be adopted for the purpose of this application, including, for example, the annulus anchors (14) disclosed in U.S. patent application Ser. No. 12/273,670 (now U.S. Pat. No. 8,951,286), filed on Nov. 19, 2008, entitled "Tissue Anchor and Anchoring System," U.S. patent application Ser. No. 11/174,951 (now U.S. Pat. No. 8,951,285), filed on Jul. 5, 2005, entitled "Tissue Anchor, Anchoring System and Methods of Using the Same," U.S. patent application Ser. No. 13/777,042 (now U.S. Pat. No. 9,259,218), filed on Feb. 26, 2013, entitled "Tissue Anchor and Anchoring System," each of which is incorporated by reference herein in its entirety. One skilled in the art should also understand that examples of suitable tissue anchors include, but not be limited to, tissue fasteners, tissue pledgets, or tissue staples etc.

As shown in FIG. 8, the proximal portion (56) of an annulus anchor (14) joins a second flexible tensioning member (16). During delivery, the second flexible tensioning member (16) is slidably disposed within the annulus anchor delivery system (60). As shown in FIG. 8, the distal end of the flexible tensioning member (16) joins the proximal portion (56) of the annulus anchor (14). The proximal end of the flexible tensioning member (16) extends proximally through the delivery system (60) and eventually to the outside of the body, and remains in the control of a clinician. As shown in FIG. 8, before the treatment is completed, a portion of the second flexible tensioning member (16) is located inside the right atrium.

Figure 10:
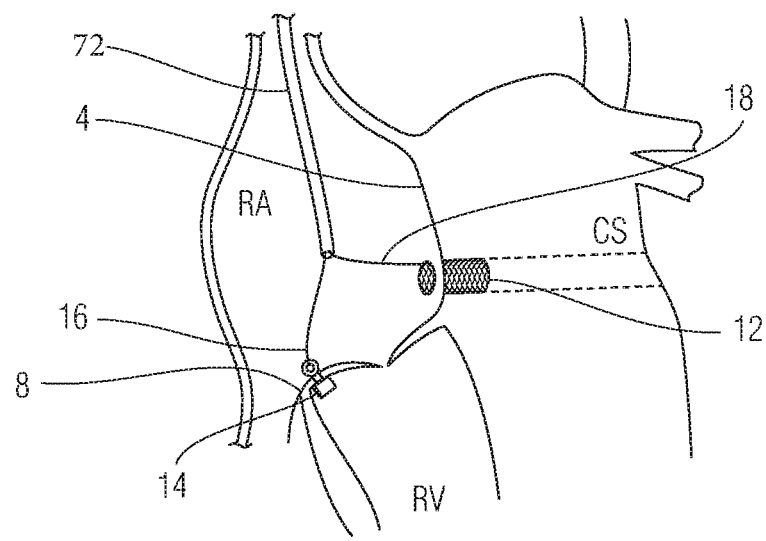
FIG. 10 is a perspective view of an embodiment of the present teachings where tension is applied to both a deployed vascular anchor and a deployed annulus anchor in accordance with the present teachings.
Figure 11:
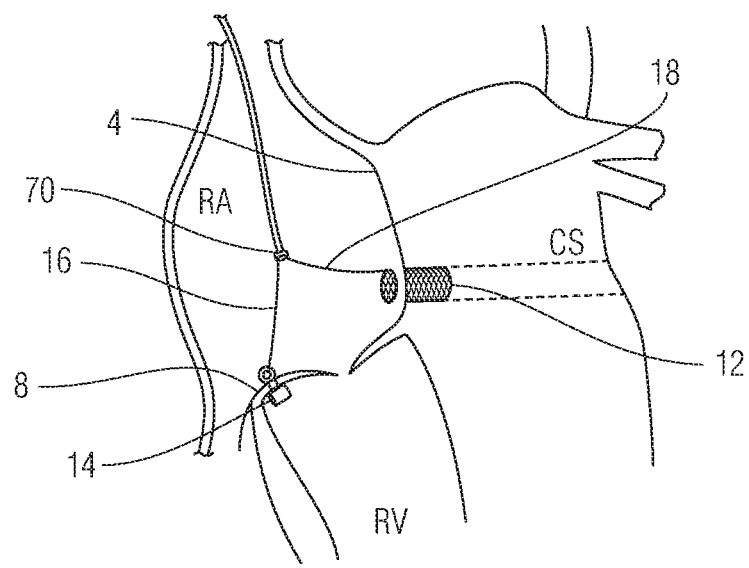
FIG. 11 is a perspective view of an embodiment of the present teachings where a deployed locking member joins both the tensioning members of a deployed vascular anchor and a deployed annulus anchor in accordance with the present teachings.

FIGS. 10-11 illustrate an embodiment of a plication procedure of the present teachings, for example, for reducing the circumference of a tricuspid valve annulus (8). Upon deployment of a vascular anchor (12) and an annulus anchor (14) at their intended locations according to the present teachings, the free ends of the tensioning members (16,18) from each anchor (12, 14) are pulled so that the anchors will be drawn towards each other to plicate the tricuspid annulus (8), as shown in FIG. 10. According to some embodiments, once both the vascular and annulus anchors (12, 14) are deployed at their respective locations, there is a first natural distance between the anchors (12, 14). Upon applying tension to both the tensioning members (16, 18) extending from the anchors (12, 14), the distance between the two anchors (12, 14) reduces to a second distance. Doing so, the natural circumference of the tricuspid annulus (8) is reduced. A crimp or other lock member (70) may then be delivered through a lock member delivery system (72) and be used to lock in the desired circumference reduction by crimping onto the tensioning members (12, 14). Upon deploying a lock member (70) in place, the excess tensioning member proximal to the lock member (70) may then be cut and removed from the body. In some embodiments, the reduction from the first natural distance to the second reduced distance is around 25-35 mm. For example, before tension is applied, the distance between both the anchors can be 25-35 mm. Upon tensioning, the distance between the two anchors is between 0-10 mm.

According to some embodiments, as shown in FIG. 11, the lock member (70) and both the tensioning members (16, 18) are located inside the right atrium after the procedure. Since the coronary sinus drains into the right atrium, and its opening locates between the inferior vena cava and the tricuspid valve on the inferior aspect of the interatrial septum (4), by pulling the anterior-posterior commissure toward the septum, in some embodiments, the tricuspid annulus (8) changes it natural shape, resulting in an improved cooptation between the anterior and posterior leaflets with the septal leaflet. In some instances, the plication achieved by the two anchors may bicuspidize the valve, creating two functioning leaflets. In some instances, the plication completely eliminates the posterior leaflet. In some instance, the plication eliminates the posterior leaflet and shortens the effective length of the septal leaflet, for example, the plication may completely obviate the posterior leaflet and may reduce the functional length of the septal leaflet by 10-15 mm.

Suitable lock members include those known in the art and those described in U.S. application Ser. No. 11/753,921 (which published as US 2007/0276437), filed on May 25, 2007, entitled "Lockers for Surgical Tensile Members and Methods of Using the Same to Secure Surgical Tensile Members," the entire disclosure of which is incorporated herein by reference. With the tensioning members secured by a lock member (not shown), the excess tensioning member(s) proximal to the lock member can be removed by a cutter, including, for example, a cutter disclosed in U.S. patent application Ser. No. 11/935,054 (now U.S. Pat. No. 8,911,461), filed on Nov. 5, 2007, entitled "Suture Cutter and Method of Cutting Suture," the entire disclosure of which is incorporated herein by reference.

Upon the deployment of the lock member (70) to lock the tensioning members in place, the circumference of the tricuspid annulus (8) is then reduced by some first reduction amount. The reduced tricuspid valve annulus therefore has lower regurgitation and allows the body to remodel.

According to some embodiments, the tensioning member (18) joins the distal end (42) of the vascular anchor (12), such as shown and described herein. One skilled in the art should understand that the tensioning member (18) could also joins the proximal end (44) of the vascular anchor (12). In some embodiments, where a vascular anchor (12) joins the tensioning member (18) at its distal end (42), the reduced tricuspid annulus (8) valve reduces and/or eliminates valve regurgitation. As the body remodels, the right atrial pressure and coronary sinus venous pressure should decrease with the decreased tricuspid valve regurgitation. This positive remodeling allows the previously dilated coronary sinus to shrink in diameter. According to some embodiments of the present teachings, the reduction in diameter of the coronary sinus causes the vascular anchor (12) to elongate, thereby reducing its diameter. As the vascular anchor (12) elongates, its distal end (42) extends further distally to the inside of the coronary sinus, applying additional tension to the tensioning member (18) connected at its distal end. This could supply additional distance reduction between the vascular anchor (12) and annulus anchor (14), thereby plicating the annulus (8) further. This effect further reduces the circumference of the tricuspid annulus (8), and further accelerates the reduction of the tricuspid valve regurgitation. According to some embodiment of the present teaching, the vascular anchor is designed with a pre-set tension limiting mechanism. Once the pre-set tension limit is reached, for example during implantation or sometimes triggered by post procedure coronary sinus remodeling, the vascular anchor will change its shape/form in part or in whole to prevent further tension increase. For example, the proximal portion of the vascular anchor could elongate under excess tension and thereby extend proximally.

Figure 12:
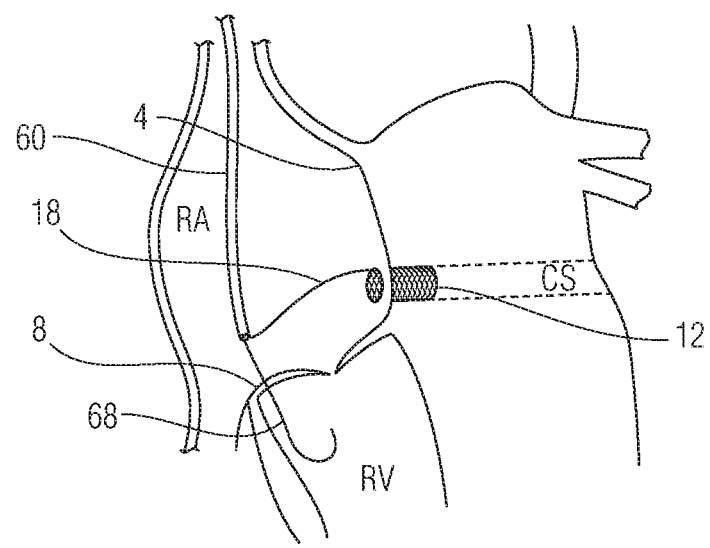
FIG. 12 is another perspective view of an exemplary positioning wire being placed across the annulus inside the right ventricle in accordance with the present teachings.
Figure 13:
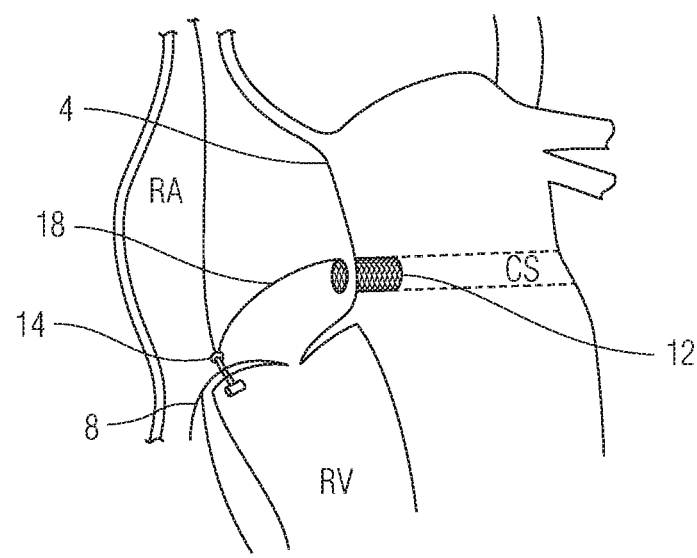
FIG. 13 is another perspective view of an exemplary annulus anchor deployed inside the right ventricle in accordance with the present teachings.
Figure 14:
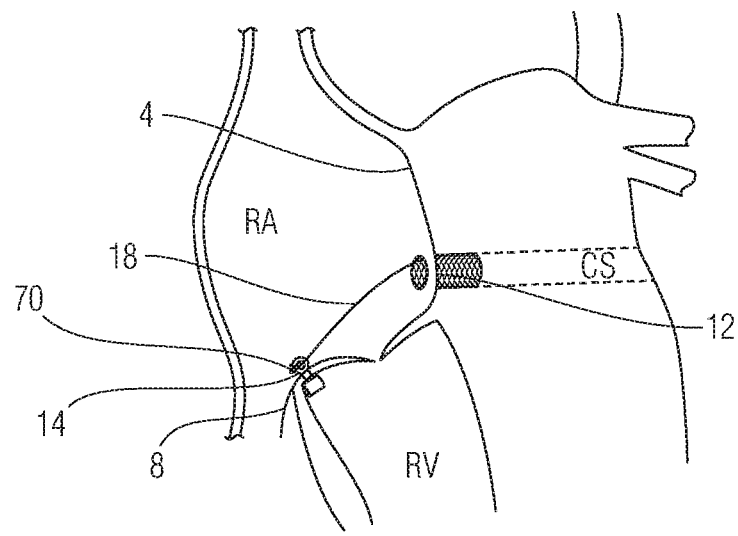
FIG. 14 is another perspective view of an embodiment of the present teachings where a locking member is deployed in accordance with the present teachings.

FIGS. 12-14 illustrate another embodiment of the present teachings, where both vascular anchor (12) and annulus anchor (14) are joined with one tensioning member (18). In this embodiment, the implantation of the vascular anchor (12) is the same as described before, for example, in relation to FIGS. 2-5. Similar to what has been described, for example, in relation to FIG. 6, a position wire (68) is then placed at a location across the tricuspid annulus (8). With the proximal end of the tensioning member (18) extending from the vascular anchor (12) to the outside of the body. A clinician then slides an annulus anchor (14) over the proximal end of the tensioning member (18), transforms the annulus anchor (14) into its collapsed delivery profile, and assembles it to the distal end portion of the annulus anchor delivery system (60). The annulus anchor delivery system assembly is similar to what has been described above for example in relation to what has been described in FIGS. 9A-9B. This assembly then tracks over the positioning wire (68) and advances distally toward the tricuspid annulus (8) implantation location as shown in FIG. 12.

Continuing referring to FIG. 13, an annulus anchor (14) is then deployed across the tricuspid annulus (8) with its distal portion (52) positioned against the annulus (8) inside the right ventricle, its central portion (54) positioned across the annulus (8), and its proximal portion (56) inside the right atrium. As shown in FIG. 13, the tensioning member (18) has its distal ends fixedly attached to the vascular anchor (12). The annulus anchor (14) has its proximal end slide over the tensioning member (18). By applying tension to the tensioning member (18), the natural distance between the annulus anchor (14) and the vascular anchor (12) is reduced, causing the annulus to plicate and/or bicuspidize. The circumference of the tricuspid annulus (8) is thereby reduced, and tricuspid regurgitation is also reduced.

Upon removing both the position wire (68) and annulus anchor delivery system (60), a tension can be applied by a clinician to the tensioning member (18), thereby pulling two anchors (16, 18) closer to each other, and effectively reducing the circumference of the tricuspid annulus (8). Then, a clinician slides a lock member (70) over the tensioning member's proximal end. Using a lock delivery system similar to what has been described above, a lock member (70) is then deployed against the annulus anchor (14), holding the pre-loaded tension on the tensioning member, maintaining the desired circumference reduction on the tricuspid annulus (8). Upon completion of the procedure, the excess tensioning member is then cut and removed from the body. FIG. 14 illustrates a vascular anchor (12) deployed inside the coronary sinus, an annulus anchor (14) deployed across the tricuspid annulus (8), and one tensioning member connecting both anchors with a lock member (70) maintaining the shortened distance between the two anchors (12, 14).

Figure 15:
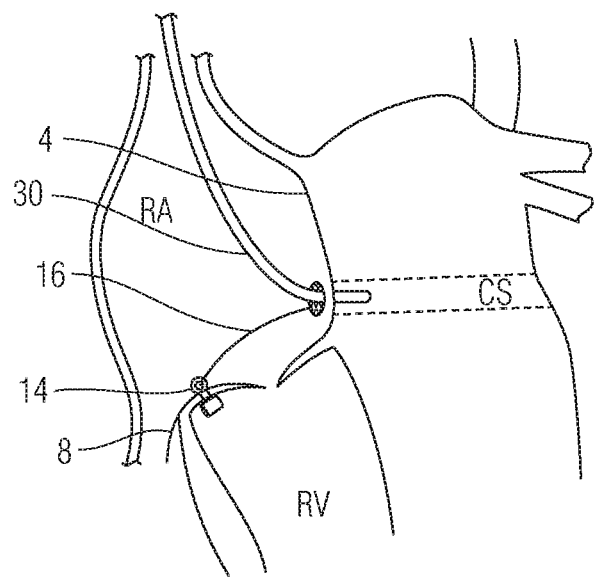
FIG. 15 is another perspective view of an exemplary vascular anchor deployed inside the right ventricle in accordance with the present teachings.
Figure 16:
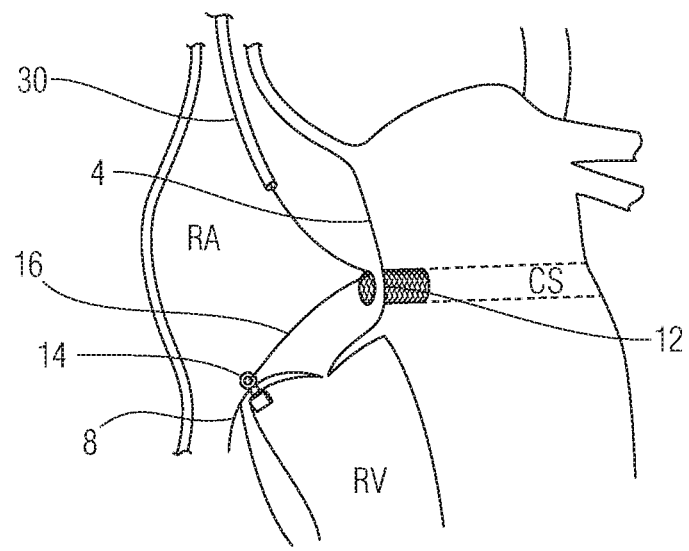
FIG. 16 is another perspective view of an exemplary vascular anchor deployed inside the right ventricle in accordance with the present teachings.

FIGS. 15-16 further illustrate another embodiment of the present teachings. Similar to the embodiments described in accordance with FIGS. 12-14, the present embodiment also involves a vascular anchor (12) and an annulus anchor (14)

joined by one tensioning member (16). In this embodiment, the annulus anchor (14) is deployed first at an identified treatment location. The procedure and methods of identifying an implantation location and deploying an annulus anchor (14) are similar to what has already been described, for example, in accordance with FIGS. 6-8.

With an annulus anchor (14) deployed across tricuspid annulus (8), a tensioning member (16) fixedly joins to the annulus anchor (14) at its proximal end, and extends proximally outside of the body. With the proximal end of the tensioning member (16) extending to the outside of the body, a clinician then slides a vascular anchor (12) over the proximal end of the tensioning member (16), then transforms the vascular anchor (12) into its collapsed delivery profile and assembles it to the distal end portion of the vascular anchor delivery system (30). The vascular anchor delivery system assembly is similar to what has been described above for example in relation to what has been described in FIGS. 3A-3B. Optionally, this assembly then tracks over the positioning wire that is put in place inside the coronary sinus. FIG. 15 illustrates that a vascular anchor delivery system assembly carrying the vascular anchor (12) advances distally, and is placed inside the coronary sinus implantation location.

The vascular anchor (12) is then deployed in accordance with what has been disclosed above. Upon deployment, as shown in FIG. 16, an annulus anchor (14) is positioned across the annulus, a vascular anchor (12) is positioned inside the coronary sinus, and a tensioning member (16) fixedly joins the annulus anchor (14) at its distal end and slides through at least a portion of the vascular anchor (12). The proximal end of the tensioning member (16) extends through at least a portion of the vascular anchor (12), and extends proximally to the outside of the body.

Figure 17:
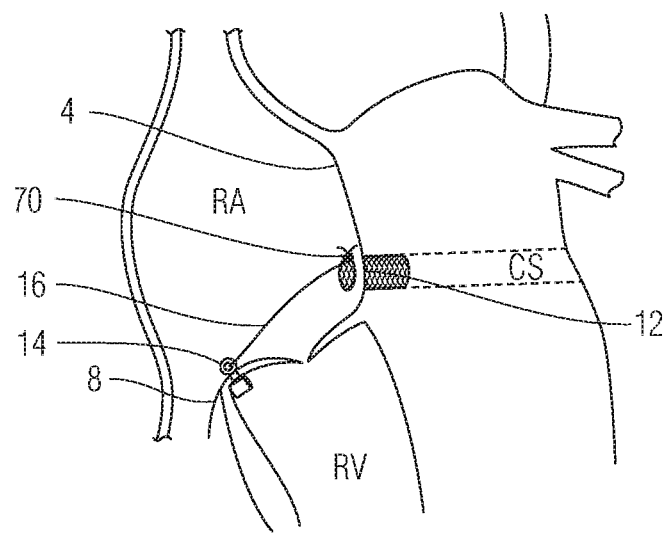
FIG. 17 is another perspective view of an embodiment of the present teachings where a locking member is deployed in accordance with the present teachings.

At this point, a tension is applied by a clinician to the tensioning member (16), thereby pulling two anchors (12, 14) closer to each other and effectively reducing the circumference of the tricuspid annulus (8). A clinician then slides a lock member (70) over the proximal end of the tensioning member (16), and uses a lock delivery system similar to what has been described above to deploy a lock member (70) against the vascular anchor (12), holding the pre-loaded tension on the tensioning member (16), maintaining the desired circumference reduction on the tricuspid annulus (8). Upon completion of the procedure, the excess tensioning member (16) is then cut and removed from the body. FIG. 17 illustrates a vascular anchor (12) deployed inside the coronary sinus, an annulus anchor (14) deployed across the tricuspid annulus (8), and one tensioning member connecting both anchors with a lock member (70) maintaining the shortened distance between the two anchors (12, 14).

Although FIGS. 1-17 illustrate embodiments of the tricuspid annulus plication system with one vascular anchor and one annulus anchor, one skilled in the art should understand that a system with one vascular anchor and more than one annulus anchor can also be applied in the treatment, and therefore such systems and uses thereof are within the scope of present teachings.

According to some embodiments, the vascular anchor has a general tubular profile, as illustrated in the figures. The vascular anchor can also have a general conical profile as disclosed above with its proximal end having a larger profile than its distal end. One skilled in the arts should understand that the vascular anchor could take on other profile that is suitable for deploying inside the coronary sinus.

Figure 18:
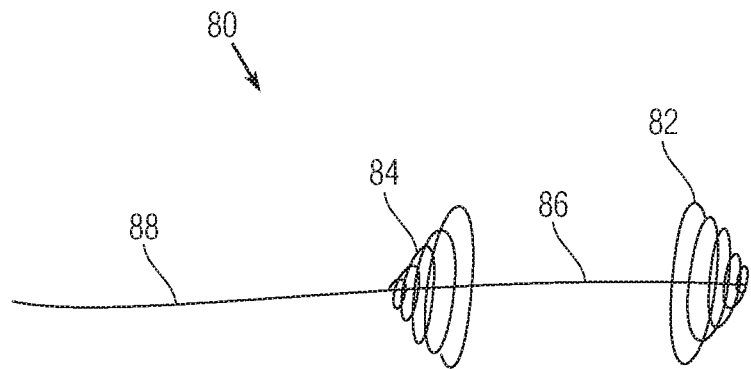
FIG. 18 is an embodiment of an exemplary vascular anchor in its deployed profile in accordance with the present teachings.
Figure 19:
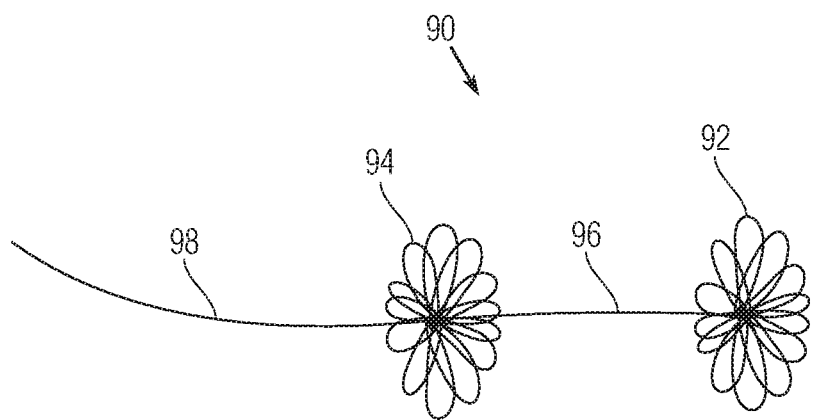
FIG. 19 is an embodiment of an exemplary vascular anchor in its deployed profile in accordance with the present teachings.

FIGS. 18-19 illustrate other embodiments of a vascular anchor (80, 90) of the present teachings. As illustrated, the vascular anchor (80, 90) has a radially enlarged distal profile (82, 92), a radially enlarged proximal profile (84, 94), and an elongated member (86, 96) connecting both the distal and proximal portions (82, 84, 92, 94). The enlarged distal portion (82, 92) could be in a shape of a cone, a disc, or other suitable profile. Similarly, the enlarged proximal portion (82, 92) could be in a shape of a cone, a disc, or other suitable profile. The elongated member (86, 96) has a smaller radial profile comparing to the distal and proximal portions (82, 84, 92, 94) of the vascular anchor (12). The elongated member (86, 96) connects the distal portion (82, 92) at its distal end, the proximal portion (84, 94) of the vascular anchor ((80, 90)) at its proximal end.

According to some embodiments, the vascular anchor (80, 90) as shown in FIGS. 18-19 are made of one continuous wire. FIG. 18 illustrates an embodiment of the present teachings where, the distal portion (82) of the wire forms a roughly spiral shape. The wire continues from the distal portion (82) of the vascular anchor (80), forms the elongated member (86), and continues toward the proximal portion (84). The proximal portion (84) of the wire also forms a roughly spiral shape. FIG. 19 illustrates another embodiment of the present teachings where, the distal and proximal portions (92, 94) of the wire forms a series of semi-circular turns which are configured to expand the inner diameter of the coronary sinus, the middle portion of the wire forms the elongated member (96) connecting the distal (92) and proximal portions (94) of the vascular anchor (90). One skilled in the art should understand FIGS. 18-19 are merely illustration of two embodiments, the vascular anchor formed of a wire can adopt other shapes and profiles for its distal and proximal portion. And the distal and proximal portions of such vascular anchor can have the same or different profiles.

In some embodiments, the wire used to form such vascular anchor is a super-elastic shape-memory wire. The shape memory wire may be pre-set into a series of large loops. The vascular anchor is delivered in a collapsed profile and once exposed inside the coronary sinus, it resumes it pre-set profile. In some embodiments, the shape memory wire has a diameter of 0.3-0.6 mm.

In one embodiment, a tensioning member (88, 98) joins the distal portion (82, 92) of the vascular anchor (80, 90). In another embodiment, a tensioning member (88, 98) joins the proximal portion of the vascular anchor (80, 90). Yet in another embodiment, the wire that forms the vascular device (80, 90) becomes a tensioning member (88, 98) that joins the vascular anchor and is used for tensioning the device.

According to various embodiments of the present teachings, a radiopaque marker or textured surface is used to make the device visible by using a radiographic imaging equipment such as an X-ray, magnetic resonance, ultrasound or other imaging technique. A marker disclosed herein may be applied to any part of the guide, catheter, or devices disclosed in present teachings. A radiopaque marker can be sewed, adhered, swaged riveted, or otherwise placed and secured on the guide, catheter, and/or devices. The radiopaque marker may be made from a material selected from tantalum, tungsten, platinum, irridium, gold, an alloy thereof, or another material known to those with ordinary skill in the art. The radiopaque marker can also be made from cobalt, fluorione, or another paramagnetic material, or another MR visible material known to those with ordinary skill in the arts. Additionally, a contrast media injected into the atrium, ventricle, or artery may also be used to confirm the positioning under a fluoroscope.

Exemplary methods for treating tricuspid valve regurgitation described herein comprises a number of other steps.

One skilled in the art should understand that the sequence of the steps can be changed, or each of steps can be omitted or modified according to each patient's needs. And those modifications should also be considered as within the scope of the present teachings. For example, access to the right atrium is gained by entering the jugular vein according to some embodiments described herein, but one skilled in the art should understand that access to the right atrium can also be achieved by entering the femoral vein and through the inferior vena cava (IVC). In addition, although the tensioning member and tissue anchor, as well as the tensioning member and vascular anchor are described as separate components according to some embodiments, one skilled in the art should understand that the tensioning member and each of the anchor can be part of an integral part. In another example, although the lock member described or incorporated above is a component separate from the tensioning member, one skilled in the art should understand other types of locking mechanisms can also be incorporated, including, for example, a knot that is part of the tensioning member and self-tightens as the tensioning member is pulled by a clinician. The present teachings also disclose certain exemplary delivery catheters/sheaths for delivering a tissue anchor, a vascular anchor, or/and a lock, and for removing a part of a tensioning member. A person skilled in the art should understand that some or all of the delivery catheters/sheaths can be combined, all of which are within the scope of this disclosure. Thus, any of the embodiments described herein should not be used to limit the scope of the invention.

Unless otherwise defined, all technical and scientific terms used herein have the same meaning as commonly understood by one of ordinary skill in the art to which this present teachings belong. Methods and materials similar or equivalent to those described herein can be used in the practice of the present teachings. In case of conflict, the specification, including definitions, controls. In addition, the materials, methods, and examples are illustrative only and not intended to be limiting.

We claim:

1. A method for use at a tricuspid valve of a heart of a subject, the tricuspid valve having an annulus and being disposed between a right atrium and a right ventricle of the heart, the heart having a coronary sinus, and the method comprising:
   using a first delivery device:
      transluminally advancing a first anchor to the coronary sinus, and
      anchoring the first anchor inside the coronary sinus;
   using a second delivery device:
      transluminally advancing a second anchor to the right atrium, the second anchor including a proximal portion, a center portion, and a distal portion that is pivotally coupled to the center portion, and
      anchoring the second anchor at a site that is across the annulus from the coronary sinus by:
         while the distal portion is disposed adjacent and parallel to the center portion, driving the distal portion from the right atrium, through the annulus at the site, and into the right ventricle,
         seating the distal portion against a ventricular surface of the annulus such that (i) the distal portion is disposed perpendicular to the center portion, (ii) the center portion extends through the annulus, and (iii) the proximal portion is disposed in the right atrium;
   while the first anchor remains anchored inside the coronary sinus and the second anchor remains anchored to the site, reducing a distance between the first and second anchors by applying tension to a tensioning member coupled to (i) the proximal portion of the second anchor and (ii) the first anchor; and
   maintaining the tension by locking a lock member to the tensioning member.

2. The method according to claim 1, further comprising sliding the lock member along the tensioning member to the right atrium subsequently to anchoring the second anchor at the site.

3. The method according to claim 1, further comprising, prior to anchoring the second anchor, forming an aperture at the site by puncturing the annulus with a wire, and wherein driving the distal portion through the annulus at the site comprises driving the distal portion through the aperture.

4. The method according to claim 1, wherein:
   transluminally advancing the second anchor to the right atrium comprises transluminally advancing the second anchor to the right atrium while the second anchor is disposed within the second delivery device, with the distal portion disposed adjacent and parallel to the center portion, and
   anchoring the second anchor at the site comprises exposing the second anchor from the second delivery device such that the distal portion pivots automatically to become disposed perpendicular to the center portion.

5. The method according to claim 1, wherein the tricuspid valve has an anterior leaflet, a septal leaflet, and a posterior leaflet, and wherein reducing the distance between the first and second anchors comprises reducing the distance between the first and second anchors such that the posterior leaflet becomes in effect eliminated.

6. The method according to claim 1, wherein:
   advancing the first anchor comprises advancing the first anchor while the first anchor is collapsed around a deflated balloon of a balloon catheter of the first delivery device, and
   anchoring the first anchor comprises plastically expanding the first anchor within the coronary sinus by inflating the balloon.

7. The method according to claim 1, wherein:
   the tensioning member is a second tensioning member, and is coupled to the first anchor via a first tensioning member,
   reducing the distance comprises reducing the distance by applying tension to the first and second tensioning members, and
   maintaining the tension comprises maintaining the tension by locking the lock member to the first and second tensioning members.

8. The method according to claim 7, wherein locking the lock member to the first and second tensioning members comprises locking the lock member to the first and second tensioning members such that the lock becomes implanted in the right atrium.

9. The method according to claim 1, wherein anchoring the first anchor inside the coronary sinus comprises anchoring the first anchor inside the coronary sinus prior to transluminally advancing the second anchor to the right atrium.

10. The method according to claim 9, wherein anchoring the first anchor inside the coronary sinus comprises anchoring the first anchor inside the coronary sinus with the tensioning member coupled to the first anchor, and wherein transluminally advancing the second anchor to the right atrium comprises sliding the second anchor over the tensioning member toward the right atrium.

11. The method according to claim 10, wherein locking the lock member to the tensioning member comprises locking the lock member to the tensioning member such that the second anchor is disposed, on the tensioning member, between the lock member and the first anchor.

12. The method according to claim 1, wherein:
translumimally advancing the first anchor to the coronary sinus comprises transluminally advancing the first anchor to the coronary sinus while the first anchor is maintained in a collapsed state within the first delivery device, and
anchoring the first anchor comprises radially expanding the first anchor within the coronary sinus.

13. The method according to claim 12, wherein anchoring the first anchor comprises ejecting the first anchor from the first delivery device within the coronary sinus such that the first anchor self-expands within the coronary sinus.

14. A method of treatment at a tricuspid valve of a heart of a subject, the tricuspid valve having an annulus and being disposed between a right atrium and a right ventricle of the heart, the heart having a coronary sinus, and the method comprising:
transluminally advancing a first anchor to the coronary sinus and anchoring the first anchor inside the coronary sinus;
transluminally advancing a second anchor to the right atrium while the second anchor is disposed within a delivery device, the second anchor including a proximal portion, a center portion, and a distal portion, and
anchoring the second anchor at a site that is across the annulus from the coronary sinus by:
driving the distal portion from the right atrium into the annulus at the site, and
exposing the second anchor from the delivery device such that the distal portion pivots automatically to become disposed orthogonal to the center portion;
while the first anchor remains anchored inside the coronary sinus and the second anchor remains anchored to the site, reducing a distance between the first and second anchors by applying tension to a tensioning member coupled to (i) the proximal portion of the second anchor and (ii) the first anchor; and
maintaining the tension by locking a lock member to the tensioning member.

15. The method according to claim 14, further comprising sliding the lock member along the tensioning member to the right atrium subsequently to anchoring the second anchor at the site.

16. The method according to claim 14, further comprising, prior to anchoring the second anchor, forming an aperture at the site by puncturing the annulus with a wire, and wherein driving the distal portion through the annulus at the site comprises driving the distal portion through the aperture.

17. The method according to claim 14, wherein the tricuspid valve has an anterior leaflet, a septal leaflet, and a posterior leaflet, and wherein reducing the distance between the first and second anchors comprises reducing the distance between the first and second anchors such that the posterior leaflet becomes in effect eliminated.

18. The method according to claim 14, wherein:
advancing the first anchor comprises advancing the first anchor while the first anchor is collapsed around a deflated balloon of a balloon catheter, and
anchoring the first anchor comprises plastically expanding the first anchor within the coronary sinus by inflating the balloon.

19. The method according to claim 14, wherein:
the tensioning member is a second tensioning member, and is coupled to the first anchor via a first tensioning member,
reducing the distance comprises reducing the distance by applying tension to the first and second tensioning members, and
maintaining the tension comprises maintaining the tension by locking the lock member to the first and second tensioning members.

* * * * *